(12) United States Patent
Hyde et al.

(10) Patent No.: US 8,116,907 B2
(45) Date of Patent: Feb. 14, 2012

(54) REORDERING OF CONSUMABLE COMPOSITIONS

(75) Inventors: Roderick A. Hyde, Redmond, WA (US);
Eric C. Leuthardt, St. Louis, MO (US);
Robert W. Lord, Seattle, WA (US);
Clarence T. Tegreene, Bellevue, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 721 days.

(21) Appl. No.: 12/217,121

(22) Filed: Jun. 30, 2008

(65) Prior Publication Data

US 2009/0143900 A1    Jun. 4, 2009

Related U.S. Application Data

(63) Continuation-in-part of application No. 11/998,461, filed on Nov. 29, 2007, and a continuation-in-part of application No. 12/001,061, filed on Dec. 7, 2007, and a continuation-in-part of application No. 12/001,063, filed on Dec. 7, 2007, now Pat. No. 7,804,419, and a continuation-in-part of application No. 12/002,794, filed on Dec. 18, 2007, and a continuation-in-part of application No. 12/004,094, filed on Dec. 19, 2007, and a continuation-in-part of application No. 12/006,252, filed on Dec. 31, 2007, and a continuation-in-part of application No. 12/012,500, filed on Dec. 1, 2008, now Pat. No. 7,919,042, and a continuation-in-part of application No. 12/074,245, filed on Feb. 29, 2008.

(51) Int. Cl.
*G06F 17/00* (2006.01)

(52) U.S. Cl. .................................... 700/236

(58) Field of Classification Search .............. 700/236
See application file for complete search history.

(56) References Cited

U.S. PATENT DOCUMENTS

| 4,223,801 | A | 9/1980 | Carlson |
| 4,310,103 | A | 1/1982 | Reilly, Jr. et al. |
| 4,641,692 | A | 2/1987 | Bennett |
| 4,899,839 | A | 2/1990 | Dessertine et al. |
| RE34,337 | E | 8/1993 | Bennett |
| 5,342,518 | A | 8/1994 | Posner et al. |
| 5,372,276 | A | 12/1994 | Daneshvar |
| 5,408,443 | A | 4/1995 | Weinberger |
| 5,454,406 | A | 10/1995 | Rejret et al. |

(Continued)

OTHER PUBLICATIONS

U.S. Appl. No. 12/927,038, Hyde et al.

*Primary Examiner* — Timothy Waggoner
(74) *Attorney, Agent, or Firm* — Suiter Swantz pc llo

(57) ABSTRACT

Methods and systems for programmed dispensation of consumable compositions are provided.
A method for administering a consumable composition may comprise one or more of the following steps: (a) dispensing a dose of a consumable composition according to a programmed dosing schedule; (b) detecting an amount of consumable composition dispensed; and (c) requesting an additional amount of consumable composition according to the amount of consumable composition dispensed.
A system for administering a consumable composition may comprise one or more of the following: (a) means for dispensing a dose of a consumable composition according to a programmed dosing schedule; (b) means for detecting an amount of consumable composition dispensed; and (c) means for requesting an additional amount of consumable composition according to the amount of consumable composition dispensed.

13 Claims, 7 Drawing Sheets

U.S. PATENT DOCUMENTS

| | | |
|---|---|---|
| 5,522,525 A | 6/1996 | McLaughlin et al. |
| 5,651,887 A | 7/1997 | Posner et al. |
| 5,681,507 A | 10/1997 | Kazuma |
| 5,752,621 A | 5/1998 | Passamante |
| 5,851,445 A | 12/1998 | Kazuma |
| 5,955,009 A | 9/1999 | Kazuma |
| 5,958,307 A | 9/1999 | Kazuma |
| 5,971,594 A | 10/1999 | Sahai et al. |
| 6,054,928 A | 4/2000 | Lemelson et al. |
| 6,068,156 A * | 5/2000 | Liff et al. ............... 700/236 |
| 6,113,080 A | 9/2000 | Kazuma |
| 6,182,453 B1 | 2/2001 | Forsberg |
| 6,249,717 B1 | 6/2001 | Nicholson et al. |
| 6,252,494 B1 | 6/2001 | Howell |
| 6,263,259 B1 * | 7/2001 | Bartur ..................... 700/236 |
| 6,330,957 B1 | 12/2001 | Bell-Greenstreet |
| 6,490,920 B1 | 12/2002 | Netzer |
| 6,529,801 B1 | 3/2003 | Rosenblum |
| 6,539,281 B2 * | 3/2003 | Wan et al. ............... 700/236 |
| 6,625,518 B2 | 9/2003 | Depeursinge |
| 6,636,780 B1 | 10/2003 | Haitin et al. |
| 6,684,920 B2 | 2/2004 | Seitz et al. |
| 6,697,704 B2 | 2/2004 | Rosenblum |
| 6,732,884 B2 | 5/2004 | Topliffe et al. |
| 6,766,218 B2 | 7/2004 | Rosenblum |
| 6,773,668 B1 | 8/2004 | Everson et al. |
| 6,856,932 B1 | 2/2005 | Wallace |
| 6,892,941 B2 | 5/2005 | Rosenblum |
| 7,072,738 B2 | 7/2006 | Bonney et al. |
| 7,175,081 B2 * | 2/2007 | Andreasson et al. ......... 700/236 |
| 7,440,818 B2 | 10/2008 | Handfield et al. |
| 7,444,203 B2 | 10/2008 | Rosenblum |
| 7,454,267 B2 | 11/2008 | Bonney et al. |
| 7,469,820 B2 | 12/2008 | Rosenblum |
| 7,471,993 B2 | 12/2008 | Rosenblum |
| 7,502,664 B2 | 3/2009 | Berg |
| 7,516,082 B2 * | 4/2009 | Sanville et al. ............ 705/8 |
| 7,630,791 B2 * | 12/2009 | Nguyen et al. ............ 700/236 |
| 7,715,277 B2 | 5/2010 | de la Huerga |
| 7,774,097 B2 | 8/2010 | Rosenblum |
| 7,831,336 B2 | 11/2010 | Gumpert |
| 2001/0011501 A1 | 8/2001 | Sato et al. |
| 2001/0045242 A1 | 11/2001 | Clusserath et al. |
| 2002/0001535 A1 | 1/2002 | Weng |
| 2002/0088817 A1 | 7/2002 | Bell-Greenstreet |
| 2003/0050731 A1 | 3/2003 | Rosenblum |
| 2003/0084957 A1 | 5/2003 | Seitz et al. |
| 2003/0088332 A1 | 5/2003 | Rosenblum |
| 2003/0093181 A1 | 5/2003 | Rosenblum |
| 2003/0220608 A1 | 11/2003 | Huitt et al. |
| 2004/0163970 A1 | 8/2004 | Sin et al. |
| 2004/0164146 A1 | 8/2004 | Rosenblum |
| 2004/0215369 A1 | 10/2004 | Rosenblum |
| 2005/0065645 A1 | 3/2005 | Liff et al. |
| 2006/0097000 A1 | 5/2006 | Gumpert |
| 2006/0259195 A1 | 10/2006 | Eliuk et al. |
| 2006/0283876 A1 | 12/2006 | Mocnik et al. |
| 2007/0184219 A1 | 8/2007 | Johnson |
| 2007/0293982 A1 | 12/2007 | Rosenblum |
| 2008/0173705 A1 | 7/2008 | Girard et al. |
| 2008/0283542 A1 | 11/2008 | Lanka et al. |
| 2009/0048712 A1 | 2/2009 | Rosenblum |
| 2009/0057341 A1 | 3/2009 | Girard et al. |
| 2009/0134181 A1 | 5/2009 | Wachman et al. |
| 2010/0324728 A1 | 12/2010 | Rosenblum |

* cited by examiner

REORDERING OF CONSUMABLE COMPOSITIONS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 11/998,461, entitled Programmed Dispensing of Consumable Compositions, naming Eric C. Leuthardt, Clarence T. Tegreene, Lowell L. Wood, Jr., Roderick A. Hyde and Robert W. Lord as inventors, filed Nov. 29, 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/001,061, entitled Programmed Dispensing of Consumable Compositions, naming Roderick A. Hyde, Eric C. Leuthardt, Robert W. Lord, Clarence T. Tegreene, and Lowell L. Wood, Jr. as inventors, filed Dec. 7, 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/001,063, entitled Programmed Dispensing of Consumable Compositions, naming Roderick A. Hyde, Eric C. Leuthardt, Robert W. Lord, Clarence T. Tegreene, and Lowell L. Wood, Jr. as inventors, filed Dec. 7, 2007 now U.S. Pat. No. 7,804,419.

For purposes of the USPTO extra-statutory requirements, the present application constitutes a continuation-in-part of U.S. patent application Ser. No. 12/002,794, entitled Communications Regarding Aspects of a Consumable Composition, naming Roderick A. Hyde, Eric C. Leuthardt, Robert W. Lord, Clarence T. Tegreene, and Lowell L. Wood, Jr. as inventors, filed Dec. 18, 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/004,094, entitled Communications Regarding Aspects of a Consumable Composition, naming Roderick A. Hyde, Eric C. Leuthardt, Robert W. Lord, Clarence T. Tegreene, and Lowell L. Wood, Jr. as inventors, filed Dec. 19, 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/006,252, entitled Sterilization of Consumable Composition Dispensers, naming Roderick A. Hyde, Eric C. Leuthardt, Robert W. Lord, Clarence T. Tegreene, and Lowell L. Wood, Jr. as inventors, filed Dec. 31, 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/012,500 entitled Sterilization of Consumable Composition Dispensers, naming Roderick A. Hyde, Eric C. Leuthardt, Robert W. Lord, Clarence T. Tegreene, and Lowell L. Wood, Jr. as inventors, filed Feb. 1, 2008 now U.S. Pat. No. 7,919,042.

For purposes of the USPTO extra-statutory requirements, the present application constitutes a continuation-in-part of United States Postal Service Express Mail No. U.S. patent application Ser. No. 12/074,245 entitled Programmed Dispensing of Consumable Compositions, naming Roderick A. Hyde, Eric C. Leuthardt, Robert W. Lord, Clarence T. Tegreene, and Lowell L. Wood, Jr. as inventors, filed Feb. 29, 2008, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

BACKGROUND

Programmed regimens of consumable compositions may be prescribed by a physician or may simply be desirable for the health and well-being of an individual. However, confusion may arise concerning the schedule, dosage, supply levels and/or compliance with a programmed dosing regimen of a consumable composition.

DETAILED DESCRIPTION

Figure 1:
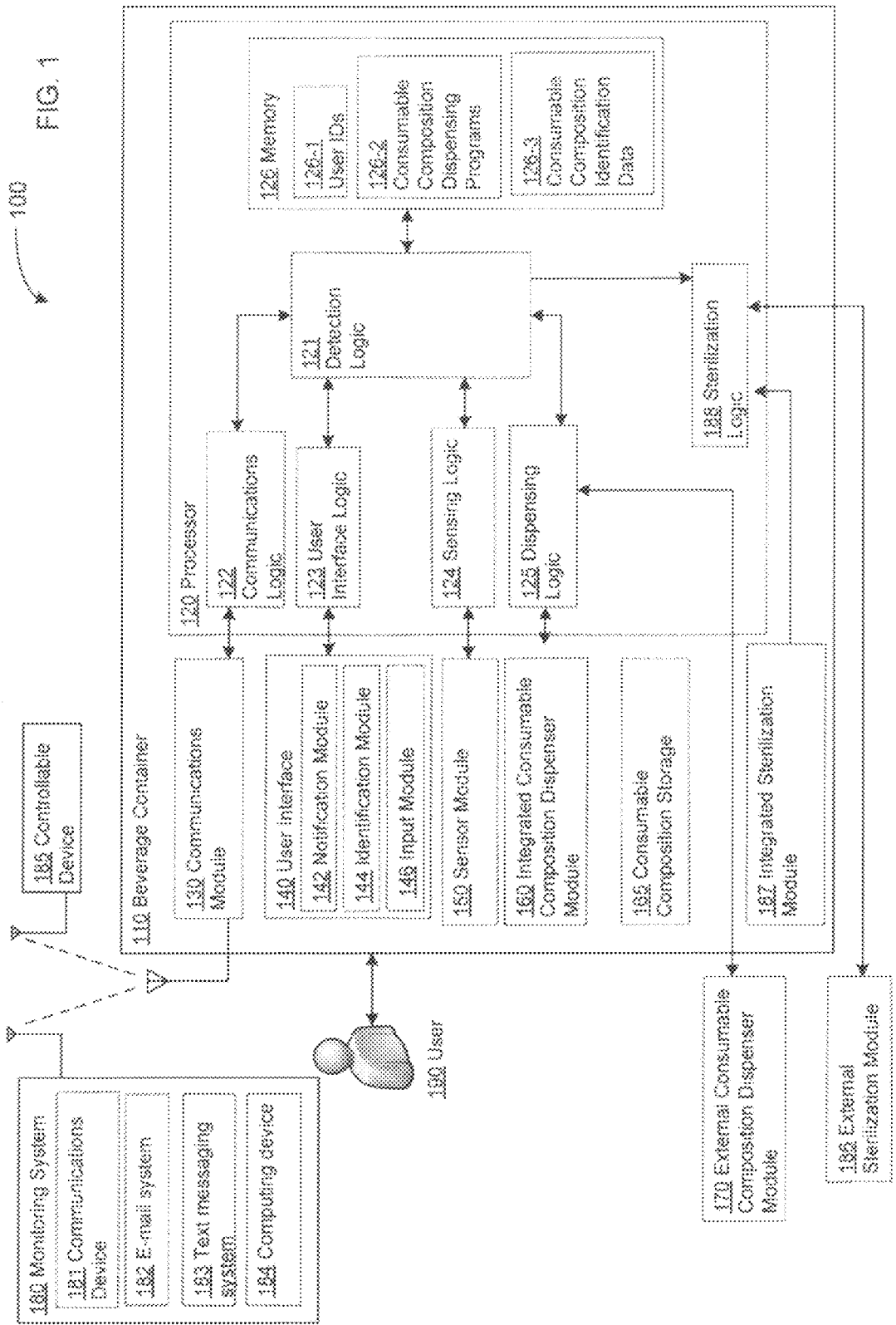
FIG. 1 shows a high-level block diagram of a beverage container.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 illustrates an example environment in which one or more technologies may be implemented. A consumable composition dispensing system 100 may comprise a beverage container 110 to be used by user 190. The beverage container 110 may be any receptacle configured for retaining a liquid or gel composition. For example, the beverage container 110 may include a cup, glass, mug, bowl, pitcher, jug, or the like.

The beverage container 110 may include a processor 120 (e.g. a microprocessor), a communications module 130 (e.g. a cellular transceiver, a Bluetooth transceiver, a WiFi transceiver, a satellite transceiver, an internet portal), a user interface 140 (e.g. display, touchscreen, keypad, speaker system), a sensor module 150 (e.g. a thermometer, barometer, concentration sensor, biometric sensor, accelerometer, UV sensor) an integrated consumable composition dispenser module 160 (e.g. injector, mechanical dispenser) and/or an integrated sterilization module 187 (e.g. a heating element).

The integrated consumable composition dispenser module 160 may be physically incorporated as a component of the beverage container 110. The integrated consumable composition dispenser module 160 may include an actuated mechanical apparatus which opens in response to a command from dispensing logic 125, thereby dispensing a dose of the consumable composition. The beverage container 110 may be configured to receive a dose of the consumable composition via gravitational flow or by pressurized injection of the dispensed composition from the integrated consumable composition dispenser module 160.

The external consumable composition dispenser module 170 may be physically separated from the beverage container 110. The external consumable composition dispenser module 170 may include a mechanical apparatus which opens in response to a command from dispensing logic 125 so as to introduce a dose of the consumable composition into the beverage container 110. The beverage container 110 may be configured to receive a dose of the consumable composition via a communicating assembly whereby the beverage container 110 may be physically coupled to the external consumable composition dispenser module 170 via a mutual conduit operably configured to allow the passage of the consumable composition between the external consumable composition dispenser module 170 and the beverage container 110.

The consumable composition dispensing system 100 may include consumable composition storage 165 (e.g. a bin, reservoir, compartment, removable cartridge, and the like). The consumable composition storage may be either integrated with or operably couplable to the internal consumable composition dispenser module 160 and/or the external consumable composition dispenser module 170 so as to provide stored doses of consumable composition for dispensing.

Processor 120 may include communications logic 122, user interface logic 123, sensing logic 124, dispensing logic 125, memory 126, and/or sterilization logic 188.

Memory 126 may include user IDs 126-1, consumable composition dispensing programs 126-2, and/or consumable composition identification data 126-3.

User interface 140 may include a notification module 142 (e.g. an LED), an identification module 144 (a fingerprint scanner), and/or an input module 146 (a microphone).

Sensor module 150 may include one or more of a light source sensor, a position sensor, an emission sensor, a spectrophotometer, an infrared or ultraviolet sensor, a biometric sensor and the like. Sensor module 150 may include a biometric sensor which senses the presence of saliva, perspiration, sebum and the like, either on the surface of the beverage container 110 or as a component of the contents therein. Sensor module 150 may include an accelerometer, an inertial motion sensor, and the like, which may sense the movement of the beverage container 110. Sensor module 150 may include a fiber optic pressure sensor, mechanical deflection pressure sensor, strain gauge pressure sensor, piezoresistive pressure sensor, microelectromechanical (MEMS) pressure sensor, variable capacitance pressure sensor, and the like which senses a pressure applied to the beverage container 110. Sensor module 150 may include a capacitive concentration sensor which may sense a concentration of the consumable composition present in the beverage container 110. Sensor module 150 may include an inclinometer and the like. Sensor module 150 may include a flowmeter for sensing a flowrate into or out of the beverage container 110. Sensor module 150 may include a capacitive level sensor, such as a strip or dual-probe sensor (e.g., a strip running down that side of the cup to sense a fluid level based at least in part between differences in the known/inferred/assumed dielectric constants of air and a fluid). In some instances, the dielectric constant is recalled/calculated in response to a sensed composition of a fluid (e.g., sensed constituents of an alcoholic cocktail); in other instances, the dielectric constant is assumed (e.g., defaults to that of water). Sensor module 150 may include an electrochemical analyzer (e.g. an electrode pair disposed within an electrolyte capable of measuring an electrochemical reaction) for measuring a concentration of a gas in an atmosphere. Sensor module 150 may include a chemical composition analysis mechanism (e.g. photoionization sensors, spectroscopic sensors, spectrometric sensors, crystallographic sensors, electrochemical sensors, calorimetric sensors).

The consumable composition dispensing system 100 may further include an external consumable composition dispenser module 170 (e.g. injector, mechanical dispenser) and/or external sterilization module 186 (e.g. an autoclave).

Monitoring system 180 may relay a notification (e.g. a notification that a sterilization of the beverage container 110 has occurred) received from communications module 130 to a communications device 181 (e.g. a cell phone, satellite phone, Blackberry®, and/or land-line phone), e-mail system 182 (e.g. an IMAP, POP3, SMTP, and/or HTTP e-mail server having an e-mail account associated with a user 190), text messaging system 183 (e.g. SMS system in GSM) and/or a computing device 184 (e.g. a personal digital assistant (PDA), personal computer, laptop, music player and/or gaming device).

The consumable composition may be a pharmaceutical composition including, but not limited to, one or more of the following: 5-alpha reductase inhibitors, 5-HT antagonists, ACE inhibitors, adrenergic agonists, adrenergic neurone blockers, alkalising agent, alpha blockers, aminoglycosides, anaesthetics, analgesics, androgens, angiotensin receptor blockers, anti-allergics, antiandrogens, antianginals, antiarrhythmics, antibiotics, anticholinergics, anticholinesterase, anticoagulants, anticonvulsants, antidepressants, antidiarrhoeals, antidopaminergics, anti-emetics, antiepileptics, antiflatulents, antifungal, antifungals, anti-hemophilics, antihistamine, antihistamines, antiplatelets, antipsychotics, antiseptics, antispasmodic, antispasmodics, antithyroid drugs, antitussives, anxiolytics, astringents, barbiturates, benzodiazepine, beta-receptor antagonists, beta-receptor blocker, bile acid sequestrants, bronchodilators, calcitonins, calcium channel blockers, cannabinoids, carbonic anhydrase inhibitors/hyperosmotics, cardiac glycosides, cerumenolyti, cholinergics, corticosteroids, COX-2 selective inhibitors, cycloplegics, cyclopyrrolone, cytoprotectants, decongestants, diphosponates, diuretics, dopamine antagonist, emetic, fibrinolytics, fluoroquinolones, gonadotropins, growth hormones, H2-receptor antagonists, haemostatic drugs, heparins, hormonal contraceptives, hypnotics, hypolipidaemic agents, imidazoles, immunoglobulins, immunosuppressants, insulin, interferons, laxatives, local anesthetics, mast cell inhibitors, miotics, monoclonal antibodies, movement disorder drugs, mucolytics, muscle relaxants, mydriatics, neuromuscular drugs, nitrates, nitroglycerin, NSAIDs, ocular lubricants, opioids, parasympatholytics, parasympathomimetics, peripheral activators, polyenes, prostaglandin agonists/prostaglandin inhibitors, prostaglandin analogues, proton pump inhibitors, quinolones, reflux suppressants, selective alpha-1 blocker, sildenafil, statins, steroids, stimulants, sulfa drugs, sympathomimetics, thyroid hormones, topical anesthetics, topical antibiotics, vaccines, vasoconstrictors, vasodilators, vasopressin analogues, or the like.

The consumable composition may be a neutraceutical composition including, but not limited to, one or more of the following: vitamins (e.g., ascorbic acid, pyridoxine, riboflavin), minerals (e.g., calcium salts, zinc salts, potassium salts), hormones (e.g., dimethylaminoethanol (DMAE), dehydroepiandrosterone (DHEA), melatonin), biochemicals (e.g., adenosine triphosphate, coenzyme A, cysteine), glandulars (e.g., edible compositions derived from glandular organs of animals such as the thyroid, pancreas, adrenal cortex), herbals (e.g., ginkgo, garlic, goldenseal, echinacea), or the like.

Figure 2:
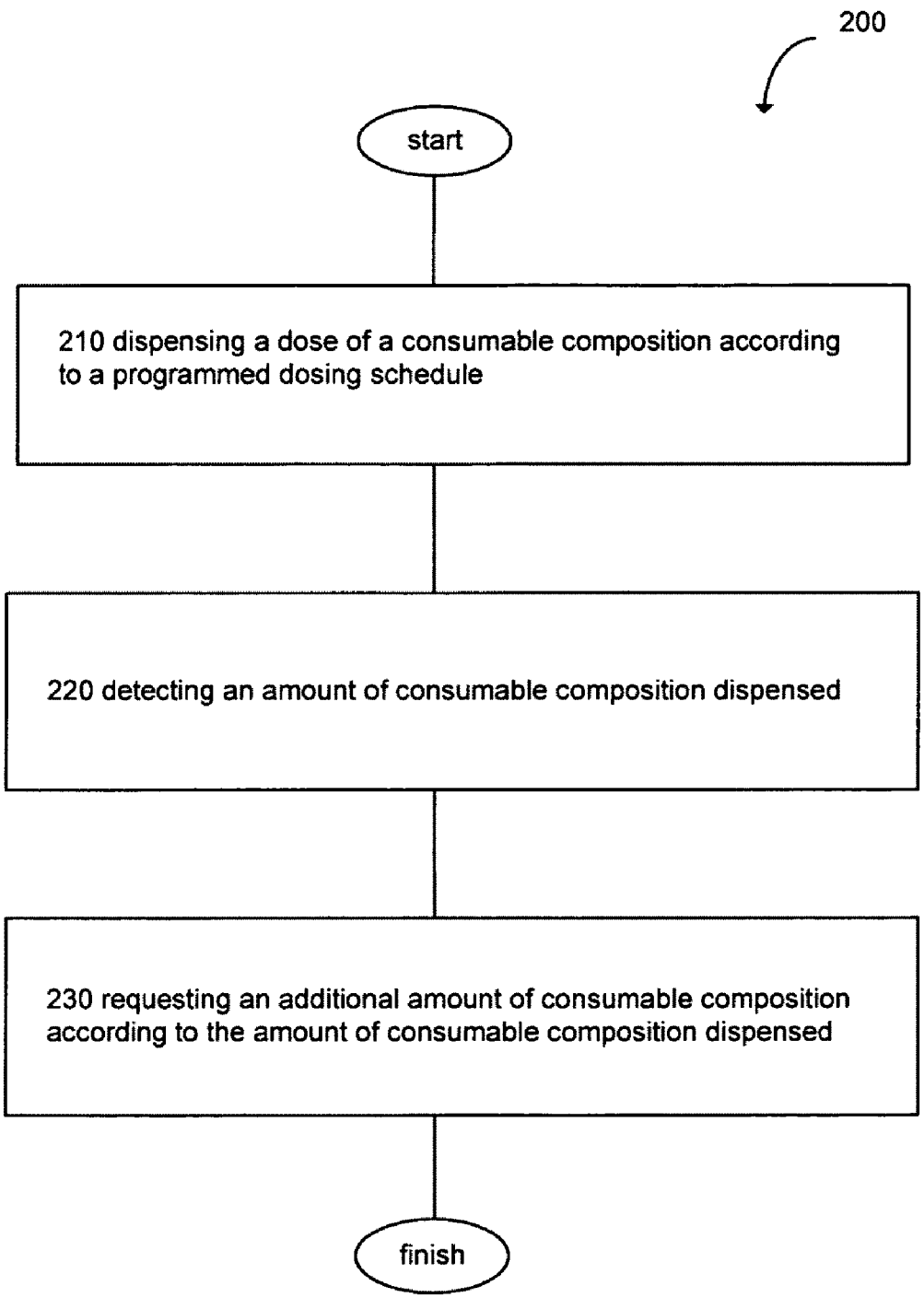
FIG. 2 is a high-level logic flowchart of a process.

FIG. 2 illustrates an operational flow 200 representing example operations related to programmed dispensing of consumable compositions. In FIG. 2 and in following figures that include various examples of operational flows, discussion and explanation may be provided with respect to the above-described examples of FIG. 1, and/or with respect to other examples and contexts. However, it should be understood that the operational flows may be executed in a number of other environments and contexts, and/or in modified versions of FIG. 1. Also, although the various operational flows are presented in the sequence(s) illustrated, it should be understood that the various operations may be performed in other orders than those which are illustrated, or may be performed concurrently.

After a start operation, the operational flow 200 may move to operation 210. Operation 210 depicts dispensing a dose of a consumable composition according to a programmed dosing schedule. For example, as shown in FIG. 1, internal consumable composition dispensing module 160 and/or external consumable composition dispensing module 170 may distribute doses of a consumable composition into a beverage container 110 according to a programmed dosing schedule (e.g. a dosing program 126-2 maintained in memory 126).

Then, operation 220 depicts detecting an amount of consumable composition dispensed. For example, as shown in FIG. 1, an amount of the consumable composition dispensed by the internal consumable composition dispenser module 160 and/or the external consumable composition dispenser module 170 may be detected by detection logic 121 receiving data from a sensing module 150 operably coupled to sensing logic 124.

Then, operation 230 depicts requesting an additional amount of consumable composition according to the amount of consumable composition dispensed. For example, once detection logic 121 has determined that a threshold amount of consumable composition has been dispensed, the communications module 130 may transmit an order for an additional amount of consumable composition to a monitoring system 180 associated with an outside entity (e.g. a consumable composition supply entity).

Figure 3:
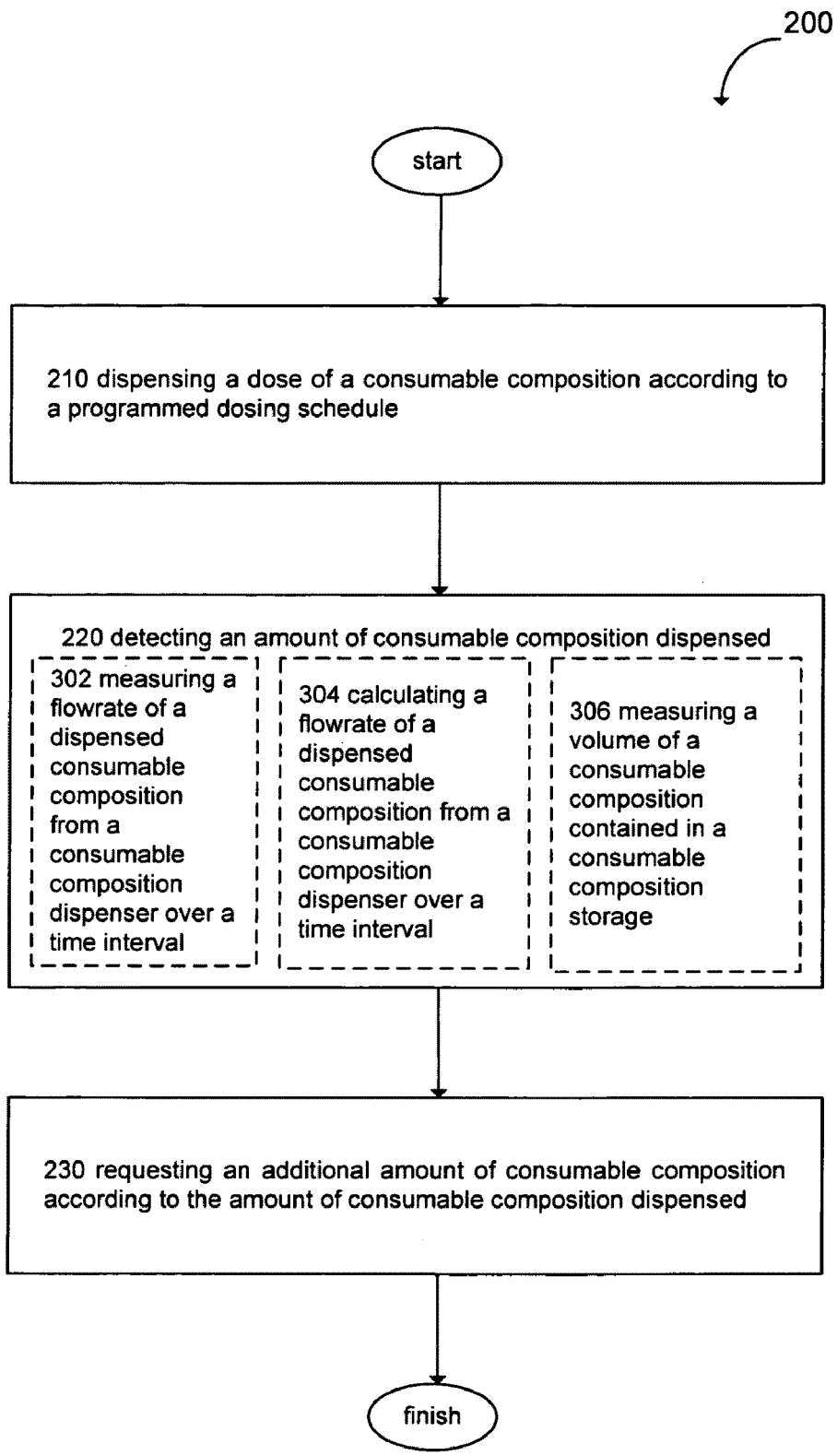
FIG. 3 is a high-level logic flowchart of a process.

FIG. 3 illustrates alternative embodiments of the example operational flow 200 of FIG. 2. FIG. 3 illustrates example embodiments where the detecting operation 220 may include at least one additional operation. Additional operations may include an operation 302, operation 304 and/or an operation 306.

Operation 302 depicts measuring a flowrate of a dispensed consumable composition from a consumable composition dispenser over a time interval (e.g. a rate at which a physical, chemical, electrical, or optical property changes). For example, as shown in FIG. 1, the sensor module 150 may include a fiber optic pressure/outflow sensor, mechanical deflection pressure/outflow sensor, strain gauge pressure/outflow sensor, piezoresistive pressure/outflow sensor, microelectromechanical (MEMS) pressure/outflow sensor, variable capacitance pressure/outflow sensor, flowmeters, and the like which sense an outflow from the beverage container 110 containing the consumable composition. Such an outflow over a given period of time may be associated with a disposal of the consumable composition, depending on the outflow rate. For example, proper ingestion might be indicated by an outflow rate indicative of normal drinking, while improper disposal might be indicated by an outflow rate indicative of dumping the contents of the cup by upending the cup.

Operation 304 depicts calculating a flowrate of a dispensed consumable composition from a consumable composition dispenser over a time interval. For example, as shown in FIG. 1, the sensor module 150 may detect a rate of change of a volume of consumable composition contained in consumable composition storage 165 (e.g. a magnetic flowmeter measuring volume outflow from the consumable composition storage 165 over time), a rate of change of a mass of consumable composition contained in consumable composition storage 165 (e.g. a piezoresistive pressure sensor measuring the change in the mass present in the consumable composition storage 165 over time), and/or a rate of change of capacitance of consumable composition contained in consumable composition storage 165 (e.g. a capacitive sensor measuring the change of capacitance of the fluid in the beverage container over time).

Operation 306 depicts measuring a volume of a consumable composition contained in a consumable composition storage (e.g. optical detection). For example, as shown in FIG. 1, the sensor module 150 may include an optical or mechanical sensor which may sense a volume of the consumable composition contained in the consumable composition storage 165.

Figure 4:
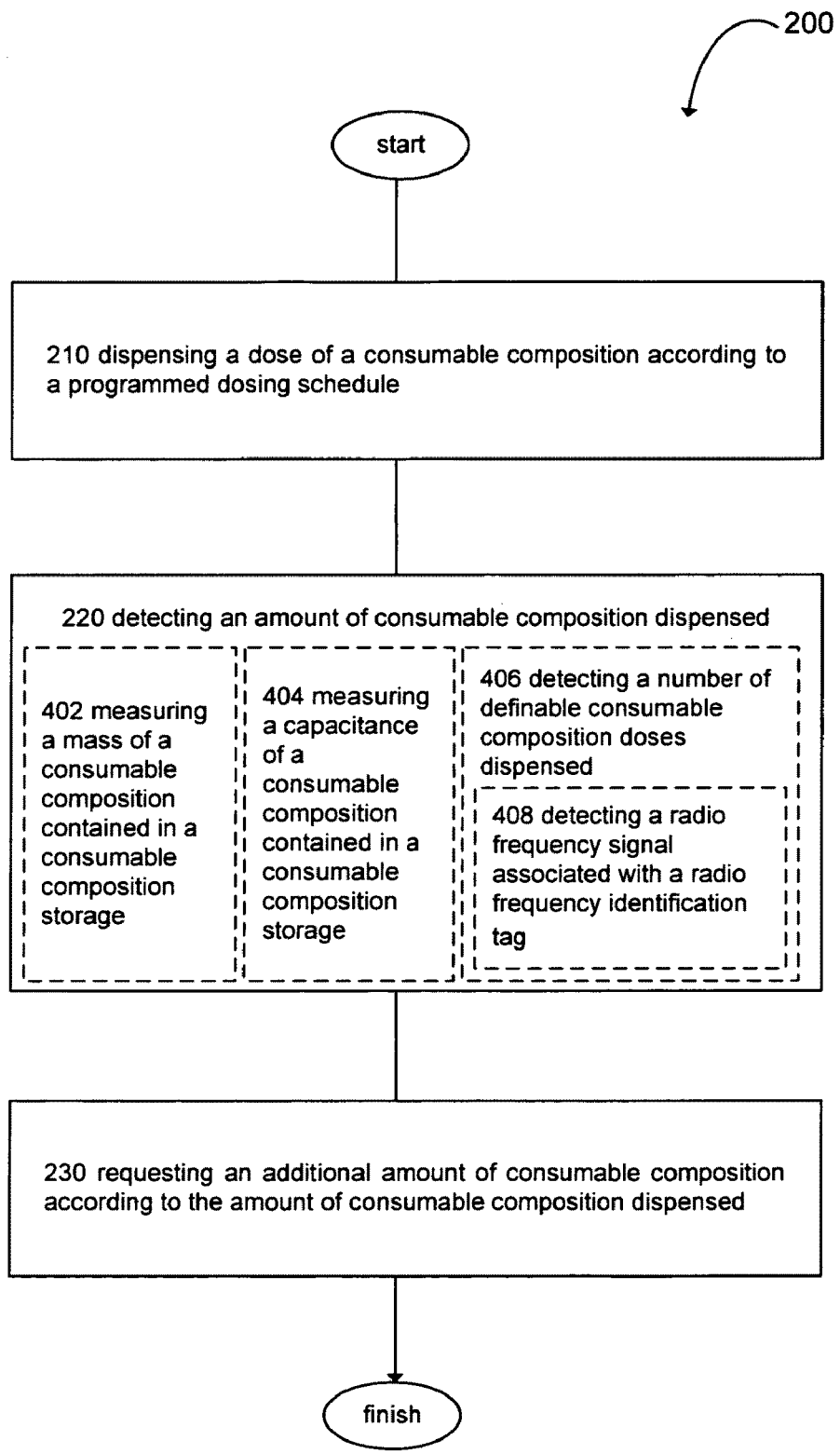
FIG. 4 is a high-level logic flowchart of a process.

FIG. 4 illustrates alternative embodiments of the example operational flow 200 of FIG. 2. FIG. 4 illustrates example embodiments where the detecting operation 220 may include at least one additional operation. Additional operations may include an operation 402 and/or an operation 404.

Operation 402 depicts measuring a mass of a consumable composition contained in a consumable composition storage (e.g. mechanical deflection pressure detection). For example, as shown in FIG. 1, the sensor module 150 may include a fiber optic pressure sensor, mechanical deflection pressure sensor, strain gauge pressure sensor, piezoresistive pressure sensor, microelectromechanical (MEMS) pressure sensor, variable capacitance pressure sensor, and the like which may sense a mass of consumable composition contained in the consumable composition storage 165.

Operation 404 depicts measuring a capacitance of a consumable composition contained in a consumable composition storage (e.g. chemical field effect transistor detection). For example, as shown in FIG. 1, the sensor module 150 may include a capacitive concentration sensor which may sense a concentration of the consumable composition contained in the consumable composition storage 165.

Operation 406 depicts detecting a number of definable consumable composition doses dispensed (e.g. detecting a number of pills dispensed). For example, as shown in FIG. 1, the sensor module 150 may include a motion sensor which may sense dispensation of a consumable composition formulated in a defined pill-type structure by the integrated consumable composition dispenser module 160 and/or the external consumable composition dispenser module 170.

Operation 408 depicts detecting a radio frequency signal associated with a radio frequency identification tag (e.g. a passive, semi-passive and/or active RFID tag). For example, as shown in FIG. 1, the sensor module 150 may include a radio frequency (RF) sensor which may transceive RF signals. The RF signals may be provided to the RF sensor by one or more RFID tags disposed within a definable dose of a consumable composition (e.g. a pill).

Figure 5:
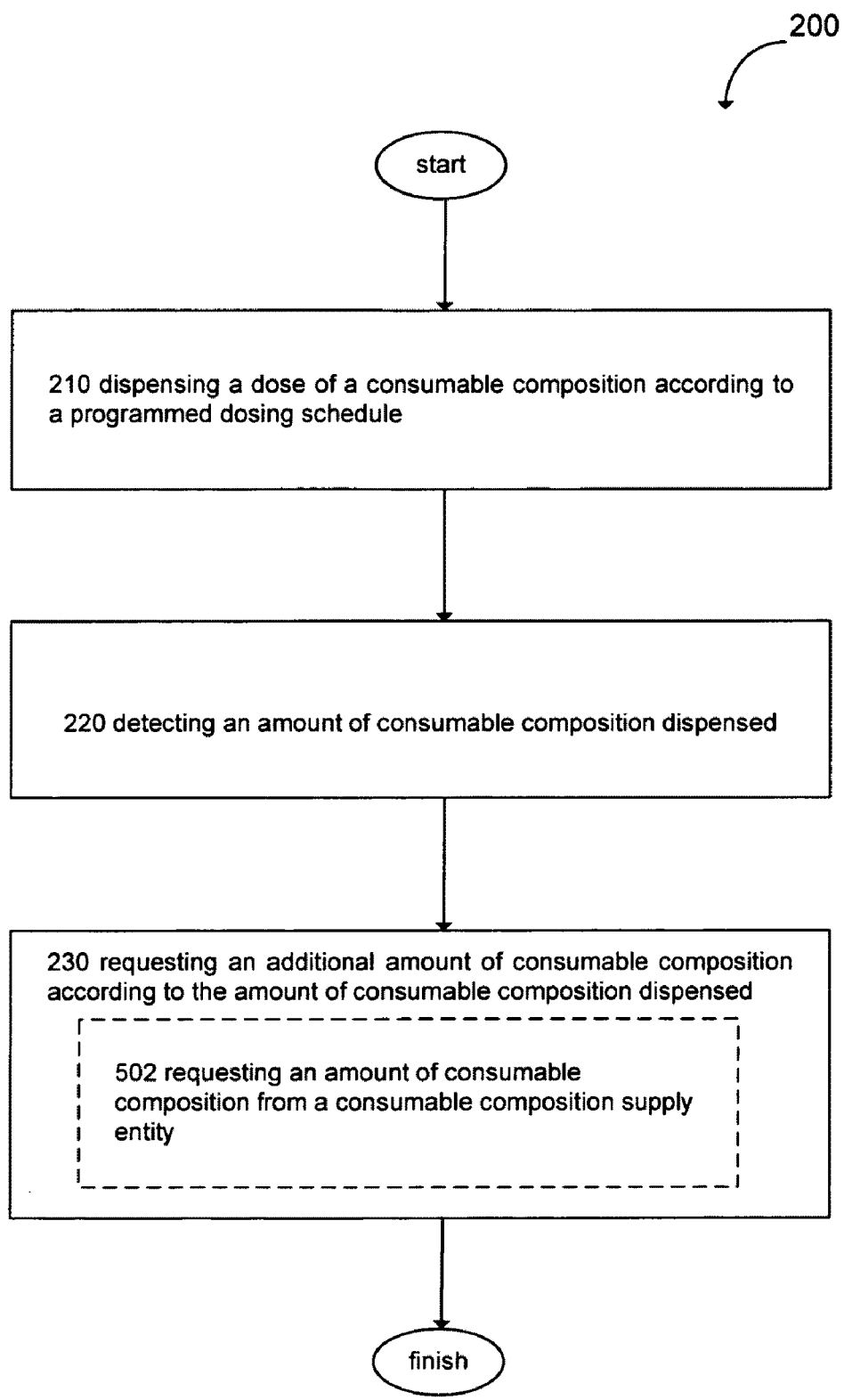
FIG. 5 is a high-level logic flowchart of a process.

FIG. 5 illustrates alternative embodiments of the example operational flow 200 of FIG. 2. FIG. 5 illustrates example embodiments where the requesting operation 230 may include at least one additional operation. Additional operations may include an operation 502.

Operation 502 depicts requesting an additional amount of consumable composition from a consumable composition supply entity. For example, once detection logic 121 has determined that a threshold amount of consumable composition has been dispensed, the communications module 130 may transmit a request for an additional amount of consumable composition to a monitoring system 180 associated with an outside entity (e.g. a consumable composition supply entity).

Figure 6:
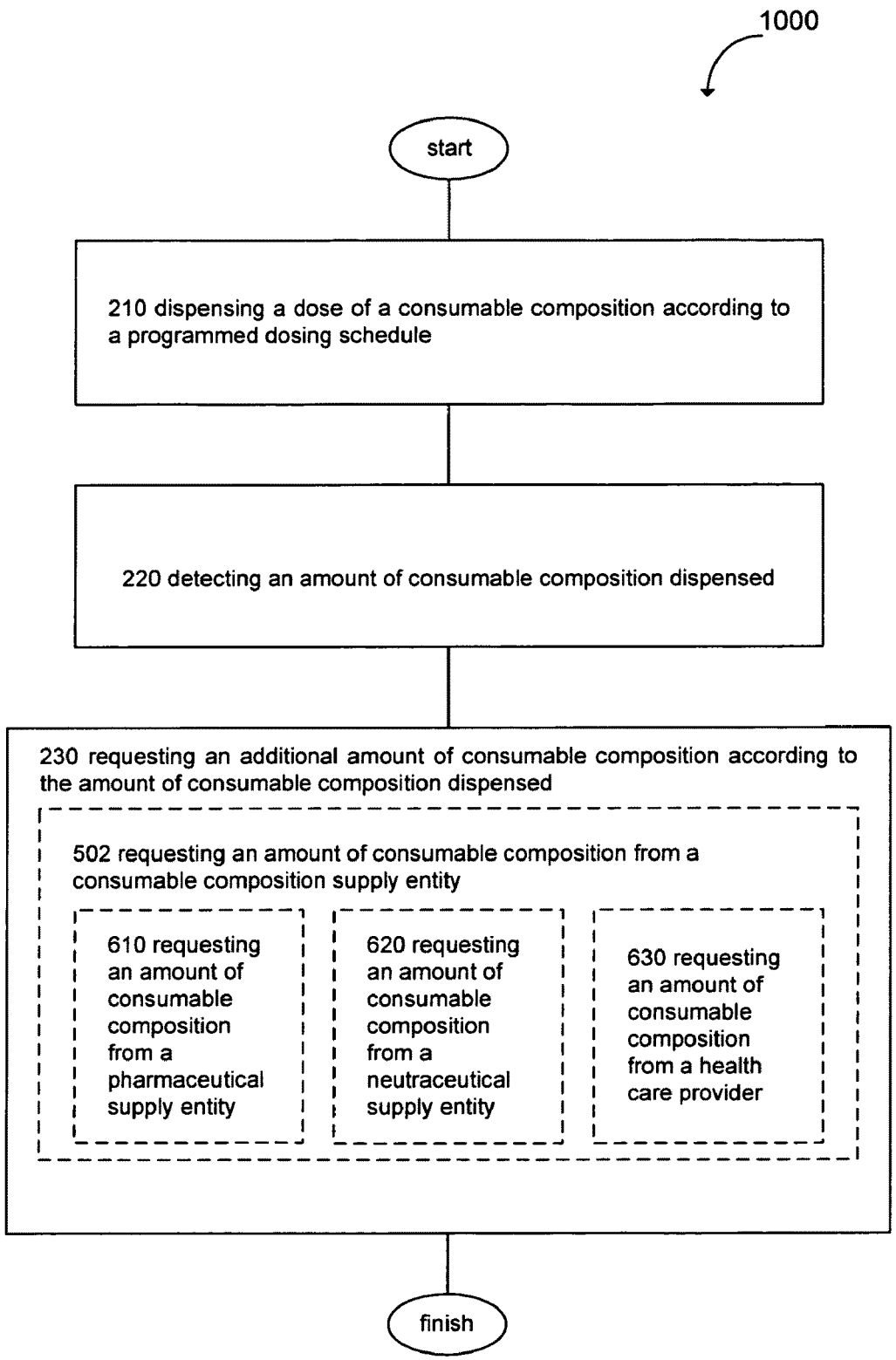
FIG. 6 is a high-level logic flowchart of a process.

FIG. 6 illustrates alternative embodiments of the example operational flow 200 of FIG. 2. FIG. 6 illustrates example embodiments where the requesting operation 502 may include at least one additional operation. Additional operations may include an operation 610, an operation 620 and/or an operation 630.

Operation 610 depicts requesting an additional amount of consumable composition from a pharmaceutical supply entity. For example, once detection logic 121 has determined that a threshold amount of a pharmaceutical composition has been dispensed, the communications module 130 may transmit a request for an additional amount of pharmaceutical composition to a monitoring system 180 associated with a pharmaceutical supply entity (e.g. an internet or telephonic ordering system for a pharmaceutical manufacturer or sales entity).

Operation 620 depicts requesting an additional amount of consumable composition from a pharmaceutical supply entity. For example, once detection logic 121 has determined that a threshold amount of a neutraceutical composition has been dispensed, the communications module 130 may transmit a request for an additional amount of neutraceutical composition to a monitoring system 180 associated with a neutraceutical supply entity (e.g. an internet or telephonic ordering system for a neutraceutical manufacturer or sales entity).

Operation 630 depicts requesting an additional amount of consumable composition from a health care provider. For example, once detection logic 121 has determined that a threshold amount of a neutraceutical composition has been dispensed, the communications module 130 may transmit a request for an additional amount of consumable composition to a monitoring system 180 associated with a health care provider (e.g. a nurses station for a hospital patient, a caregiver in an assisted living facility, a prescribing physician, and the like).

Figure 7:
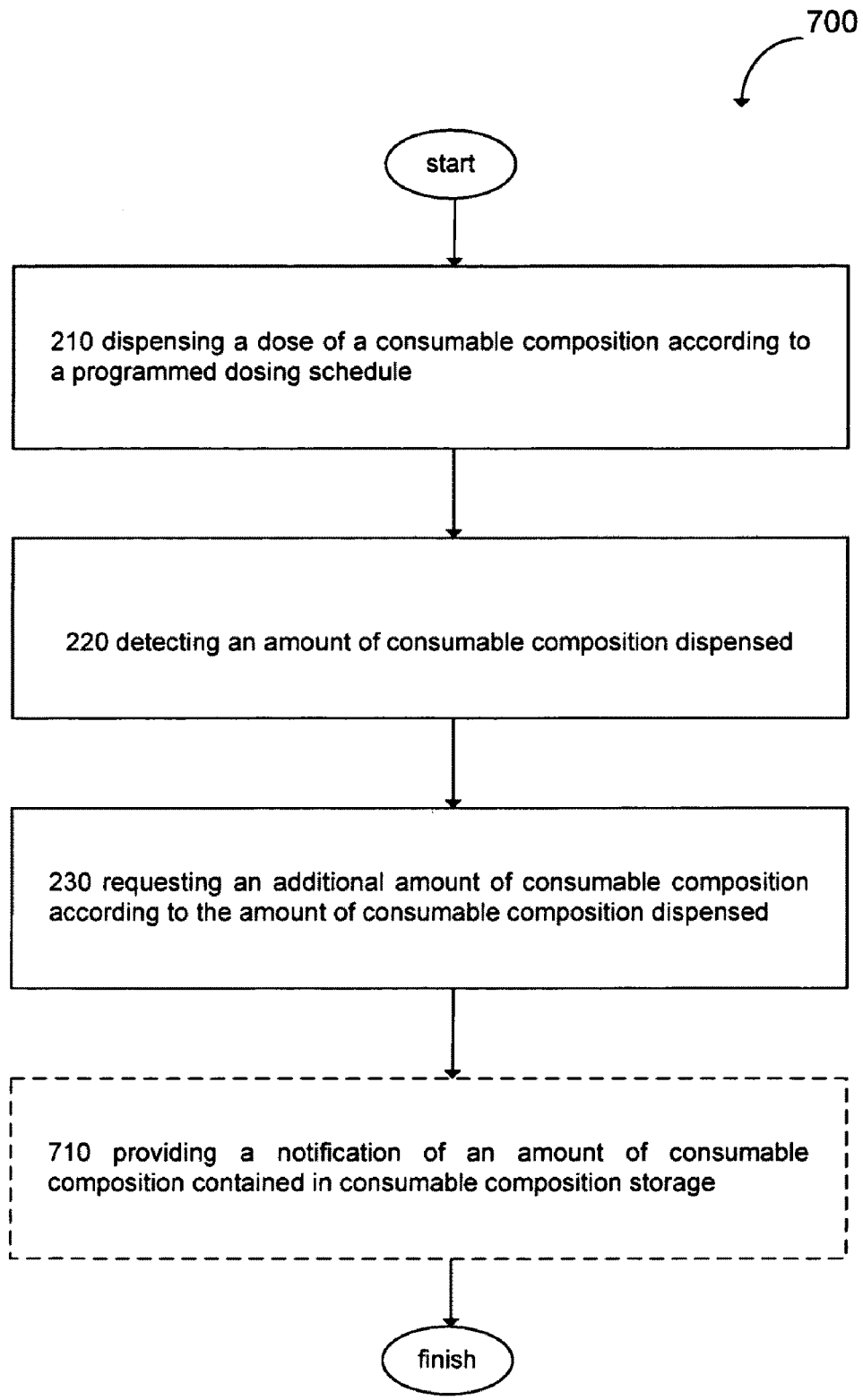
FIG. 7 is a high-level logic flowchart of a process.

FIG. 7 illustrates an operational flow 700 representing example operations related to programmed dispensing of consumable compositions. FIG. 7 illustrates an example embodiment where the example operational flow 200 of FIG. 2 may include at least one additional operation. Additional operations may include an operation 702.

Operation 702 depicts providing a notification of an amount of consumable composition dispensed. For example, as shown in FIG. 1, the user interface logic 123 may cause the notification module 142 of the user interface 140 to provide a notification of an amount of the consumable composition that has been dispensed. The notification may include a visual (e.g. flashing LED, LCD display screen, etc.), audible (e.g. speaker assembly), or tactile (e.g. vibratory) notification.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, e.g., transmitter, receiver, transmission logic, reception logic, etc.), etc.).

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into an image processing system. Those having skill in the art will recognize that a typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

What is claimed is:

1. A system for administering a consumable composition, the system comprising:
    means for dispensing a dose of a consumable composition according to a programmed dosing schedule;
    means for detecting an amount of consumable composition dispensed; and
    means for requesting an additional amount of consumable composition according to the amount of consumable composition dispensed.

2. The system of claim 1, wherein the means for detecting an amount of consumable composition dispensed further comprises:
    means for measuring a flowrate of a dispensed consumable composition from a consumable composition dispenser over a time interval.

3. The system of claim 1, wherein the means for detecting an amount of consumable composition dispensed further comprises:
    means for calculating a flowrate of a dispensed consumable composition from a consumable composition dispenser over a time interval.

4. The system of claim 1, wherein the means for detecting an amount of consumable composition dispensed further comprises:
    means for measuring a volume of a consumable composition contained in a consumable composition storage.

5. The system of claim 1, wherein the means for detecting an amount of consumable composition dispensed further comprises:
    means for measuring a mass of a consumable composition contained in a consumable composition storage.

6. The system of claim 1, wherein the means for detecting an amount of consumable composition dispensed further comprises:
    means for measuring a capacitance of a consumable composition contained in a consumable composition storage.

7. The system of claim 1, wherein the means for detecting an amount of consumable composition dispensed further comprises:
    means for detecting a number of definable consumable composition doses dispensed.

8. The system of claim 7, wherein the means for detecting a number of definable consumable composition doses dispensed further comprises:
    means for detecting a radio frequency signal associated with a radio frequency identification tag.

9. The system of claim 1, wherein the means for requesting an additional amount of consumable composition according to the amount of consumable composition dispensed comprises:
    means for requesting an additional amount of consumable composition from a consumable composition supply entity.

10. The system of claim 9, wherein the means for requesting an additional amount of consumable composition from a consumable composition supply entity comprises:
    means for requesting an additional amount of consumable composition from a pharmaceutical supply entity.

11. The system of claim 9, wherein the means for requesting an additional amount of consumable composition from a consumable composition supply entity comprises:
   means for requesting an additional amount of consumable composition from a neutraceutical supply entity.

12. The system of claim 9, wherein the means for requesting an additional amount of consumable composition from a consumable composition supply entity comprises:
   means for requesting an additional amount of consumable composition from a health care provider.

13. The system of claim 9, further comprising:
   means for providing a notification of an amount of consumable composition dispensed.

\* \* \* \* \*